United States Patent [19]

Picataggio et al.

[11] Patent Number: 5,648,247
[45] Date of Patent: Jul. 15, 1997

[54] METHOD FOR INCREASING THE OMEGA-HYDROXYLASE ACTIVITY IN CANDIDA TROPICALS

[75] Inventors: Stephen Picataggio, Santa Rosa; Tracy Rohrer, Cotati; L. Dudley Eirich, Santa Rosa, all of Calif.

[73] Assignee: Henkel Corporation, Plymouth Meeting, Pa.

[21] Appl. No.: 425,124

[22] Filed: Apr. 19, 1995

Related U.S. Application Data

[63] Continuation of Ser. No. 975,154, Nov. 12, 1992, abandoned, which is a continuation of Ser. No. 495,502, Mar. 19, 1990, abandoned.

[51] Int. Cl.[6] .............................. C12P 7/44; C12N 1/16
[52] U.S. Cl. .............................. 435/142; 435/254.22
[58] Field of Search ........................ 435/172.3, 69.1, 435/142, 254.22; 535/23.2, 23.74

[56] References Cited

U.S. PATENT DOCUMENTS

| | | | |
|---|---|---|---|
| 3,975,234 | 8/1976 | Hitzman | 435/142 |
| 4,339,536 | 7/1982 | Kato et al. | 435/142 |
| 4,474,882 | 10/1984 | Kunishige et al. | 435/142 |

FOREIGN PATENT DOCUMENTS

| | | |
|---|---|---|
| 2164626 | 11/1972 | Germany. |
| 2140133 | 2/1973 | Germany. |
| 2853847 | 6/1979 | Germany. |
| 2937292 | 4/1980 | Germany. |
| 2951177 | 7/1980 | Germany. |
| 1405026 | 9/1975 | United Kingdom. |

OTHER PUBLICATIONS

Liskay et al., 1987, Genetics, vol. 115: 161–167.
Okazaki et al. Gene 57:37–44 (1987).
Okazaki et al. Biochem 83:1232 (1986).
Sanglard et al. Gene 76:121 (1989).
Sanglard "FEBS lett." 256:128 (1989).
Sanglard "Experientia" 49: 1983, #Gen 418 (1988).
Loper "Genetics" 113:Suppl. No. 1, P+2, 514 #2.18 (1986).
Loper et al. U.S. Envir. Prot. Agency Res Dev 1984. Abstract only.
ATCC catalogue 7th Ed. 1987 (Fergi +Yeaki) p. 80.
Kelly et al. Mol. Cell Biol Jan 1987: 199.
Gillum et al. Mol. Gen Genet 198:179 (1984).
Strommae et al. J. Bact Jan. 1986:197.
Aitchardin et al. Chem Abstr. 77(23): No. 149584A (1971).
Gaillardin et al. Chem Abstr. 77(23):No. 149584A (1971).
Wataabe et al. Chem Abstr. 70(15):No. 65372n (1968).
Small et al. J. Cell Biol 105:247 (1987).
Acta Microbiol. Sim. 21:88–95 (1981), Abstract only.
*Agr. Biol. Chem.* 35 2033–2042 (1971) Shiio et al., "Microbial Production of Long–Chain Dicarboxylic Acids from n–Alkanes".
Lawrence et al. (eds) *Flavors and Fragrances: A World Perspective* (1988) Okino et al., "Production of Macrocyclic Musk Compounds . . . from n–Alkanes".
*Aliphatic Hydrocarbons in Biotechnology*, vol. 6a, Verlag Chemie, Weinheim (1984) Buehler et al.
Gilewicz et al., *Can. J. Microbiol.*, 25 pp. 201–206 (1979), "Hydroxylase regulation in Candida tropicalis grown on alkanes".
Sanglard & Loper, *Gene* 76, 121–136 (1989), "Characterization of the alkane–inducible cytochrome P450 (P450 alk) gene from the yeast *Candida tropicalis*".

(List continued on next page.)

*Primary Examiner*—David Guzo
*Assistant Examiner*—Robert Schwartzmann
*Attorney, Agent, or Firm*—Wayne C. Jaeschke; John E. Drach; Jeffrey S. Steen

[57] ABSTRACT

The omega-hydroxylase activity in the yeast *Candida tropicalis* is increased by amplification of the P450ALK and P450RED genes. The specific productivity (grams of dicarboxylic acid/liter/hr) of substantially pure alpha, omega-dicarboxylic acids is increased by culturing *C. tropicalis* strains having amplified P450ALK and P450RED genes.

74 Claims, 5 Drawing Sheets

OTHER PUBLICATIONS

Kemp et al., *Appl. Microbiol. and Biotechnol*, 29 pp. 370–374 (1988) "Inducible long chain alcohol oxidase from alkane-grown *Candida tropicalis*".

*J. Biochem.*, 102 225–234 (1987) Vamecq et al., "Interactions between the ω–and β–Oxidations of Fatty Acids".

*Agr. Biol. Chem.*, 49 1821–1828 (1985), Ueda et al. "Peroxisomal Localization of Enzymes Related to Fatty Acid β–Oxidation in . . . *Candida tropicalis*".

P450-AMPLIFICATION VECTORS
CYTOCHROME P450:
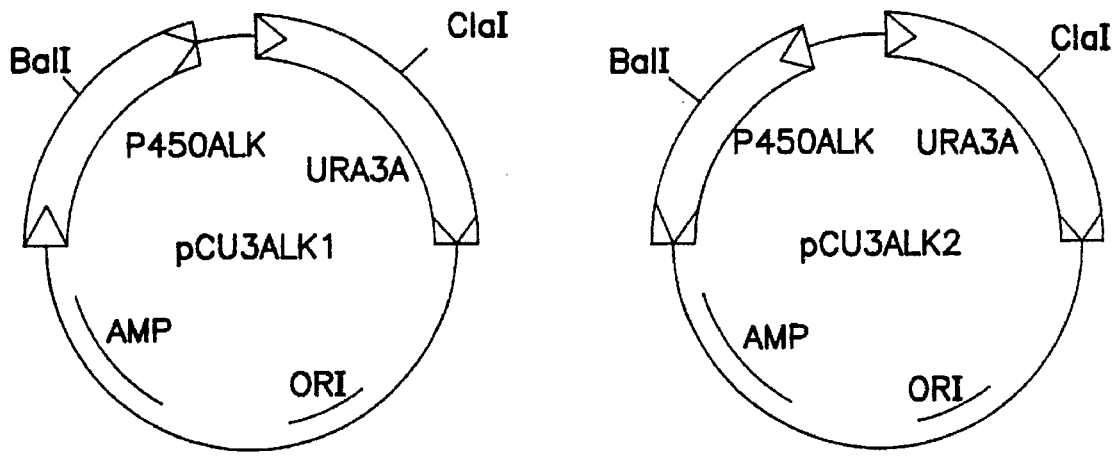
NADPH REDUCTASE:
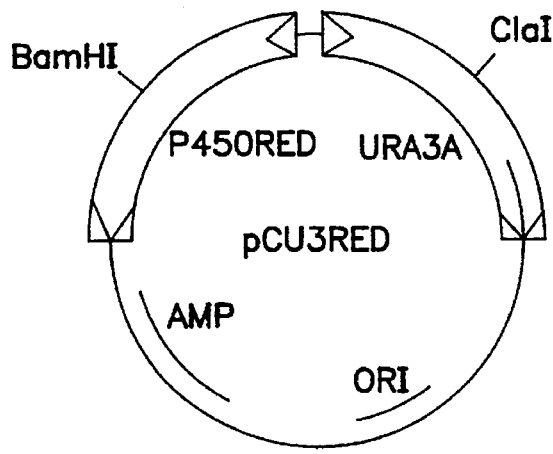
FIG. 1

P450 AMPLIFICATION STRATEGY IN β-OXIDATION BLOCKED STRAINS OF C. tropicalis

ω-HYDROXYLASE AMPLIFIED STRAINS[1]

| STRAIN | GENE[2] | TANDEM INTEGRATIONS | ω-HYDROXYLASE ACTIVITY[3] | REDUCTASE ACTIVITY[4] |
|---|---|---|---|---|
| SU-2 | — | — | 0.145 | 1.15 |
| SA1C1 | P450ALK1 | SINGLE | 0.214 | 2.29 |
| SA1C2 | P450ALK1 | DOUBLE | 0.223 | 3.08 |
| SA1CM | P450ALK1 | MULTIPLE | 0.117 | 1.74 |
| SA2C1a | P450ALK2 | SINGLE | 0.206 | 2.07 |
| SA2CM | P450ALK2 | MULTIPLE | 0.242 | 2.13 |
| SRC1 | P450RED | SINGLE | 0.226 | 3.42 |
| SRCM | P450RED | MULTIPLE | 0.409 | 8.03 |

1  derived from Strain SU-2

2  P450ALK1 = Cytochrome P450 gene
   P450ALK2 = Cytochrome P450 gene in opposite orientation
   P450RED  = NADPH cytochrome P450 reductase gene 3  % lauric acid conversion/μg 4  Δ A/min/mg

FIG. 3

ω-HYDROXYLASE AMPLIFIED STRAINS[1]

| STRAIN | Estimated Number of Integrations | | | ω-HYDROXYLASE ACTIVITY[2] | REDUCTASE ACTIVITY[3] |
|---|---|---|---|---|---|
| | P450 ALK | P450 RED | | | |
| Oxidation Blocked | | | | | |
| H5343 | — | — | | 0.125 | 1.13 |
| Cytochrome Amplified | | | | | |
| A2 | 1 | — | | 0.092 | 1.25 |
| A4 | 2 | — | | 0.074 | 0.77 |
| A1 | Multiple | — | | 0.053 | 0.97 |
| Reductase Amplified | | | | | |
| R20 | — | 1 | | 0.107 | 1.58 |
| R12 | — | 2 | | 0.146 | 3.06 |
| R24 | — | Multiple | | 0.161 | 5.34 |
| Both Amplified | | | | | |
| AR25 | 2 | 2 | | 0.191 | 2.08 |
| AR40 | 3 | 2 | | 0.243 | 3.23 |
| AR42 | Multiple | Multiple | | 0.400 | 6.26 |
| COR34 | 1 | Multiple | | 0.285 | 5.05 |
| COR5 | 2 | Multiple | | 0.186 | 5.92 |

1 Derived from Strain H5343
2 % lauric acid conversion/μg
3 ΔA/min/mg

FIG. 4

METHOD FOR INCREASING THE OMEGA-HYDROXYLASE ACTIVITY IN CANDIDA TROPICALS

This application is a continuation of application Ser. No. 07/975,154, filed on Nov. 12, 1992, which is a continuation of Ser. No. 07/495,502, filed on Mar. 19, 1990, both abandoned.

BACKGROUND OF THE INVENTION

1. Field of the Invention

This invention relates to a method for increasing the omega-hydroxylase activity in the yeast *Candida tropicalis*. This invention also relates to *C. tropicalis* strains having increased omega-hydroxylase activity and to a method of using these strains for the production of dicarboxylic acids.

2. Description of the Related Art

Aliphatic dioic acids are versatile chemical intermediates useful as raw materials for the preparation of perfumes, polymers, adhesives and macrolid antibiotics. While several chemical routes to the synthesis of long-chain alpha, omega dicarboxylic acids are available, the synthesis is not easy and most methods result in mixtures containing shorter chain lengths. As a result, extensive purification steps are necessary. While it is known that long-chain dioic acids can also be produced by microbial transformation of alkanes, fatty acids or esters thereof, chemical synthesis has remained the preferred route, due to limitations with the current biological approaches.

Several strains of yeast are known to excrete alpha, omega-dicarboxylic acids as a byproduct when cultured on alkanes or fatty acids as the carbon source. In particular, yeast belonging to the Genus Candida, such as *C. albicans, C. cloacae, C. guillermondii, C. intermedia, C. lipolytica, C. maltosa, C. parapsilosis* and *C. zeylenoides* are known to produce such dicarboxylic acids (Agr. Biol. Chem. 35; 2033–2042 (1971)). Also, various strains of *C. tropicalis* are known to produce dicarboxylic acids ranging in chain lengths from $C_{11}$ through $C_{18}$ (Okino et al., In BM Lawrence, BD Mookherjee and BJ Willis (eds), Flavors and Fragrances: A World Perspective. Proceedings of the 10$^{th}$ International Conference of Essential Oils, Flavors and Fragrances, Elsevier Science Publishers BV Amsterdam (1988)), and are the basis of several patents as reviewed by Behler and Schindler, in Aliphatic Hydrocarbons in Biotechnology, H. J. Rehm and G. Reed (eds), Vol. 169, Verlag Chemie, Weinheim (1984).

Studies of the biochemical processes by which yeasts metabolize alkanes and fatty acids have revealed three types of oxidation reactions: α-oxidation of alkanes to alcohols, omega-oxidation of fatty acids to alpha, omega-dicarboxylic acids and the degradative β-oxidation of fatty acids to $CO_2$ and water. The first two types of oxidations are catalyzed by microsomal enzymes while the last type takes place in the peroxisomes. In *C. tropicalis*, the first step in the omega-oxidation pathway is catalyzed by a membrane-bound enzyme complex (omega-hydroxylase complex) comprised of a cytochrome P450 monooxygenase and a NADPH-cytochrome reductase. This hydroxylase complex is responsible for the primary oxidation of the terminal methyl group in alkanes and fatty acids (Gilewicz et al., Can. J. Microbiol., 25, p 201 (1979)). The genes which encode the cytochrome P450 and NADPH reductase components of the complex have been identified as P450ALK and P450RED respectively, and have also been cloned and sequenced (Sanglard and Loper, Gene 76, 121–136 (1989)). Fatty acids are ultimately formed from alkanes after two additional oxidation steps, catalyzed by alcohol oxidase (Kemp et al., Appl. Microbiol. and Biotechnol, 28, p370–374 (1988)) and aldehyde dehydrogenase. The fatty acids can be further oxidized through the same or similar pathway to the corresponding dicarboxylic acid. The omega-oxidation of fatty acids proceeds via the omega-hydroxy fatty acid and its aldehyde derivative, to the corresponding dicarboxylic acid without the requirement for CoA activation. However, both fatty acids and dicarboxylic acids can be degraded, after activation to the corresponding acyl-CoA ester through the β-oxidation pathway in the peroxisomes, leading to chain shortening. In mammalian systems, both fatty acid and dicarboxylic acid products of omega-oxidation are activated to their CoA-esters at equal rates and are substrates for both mitochondrial and peroxisomal β-oxidation (J.Biochem., 102, 225–234 (1987)). In yeast, β-oxidation takes place solely in the peroxisomes (Agr. Biol. Chem., 49, 1821–1828 (1985)).

The production of dicarboxylic acids by fermentation of unsaturated $C_{14}$–$C_{16}$ monocarboxylic acids using a strain of the species *C. tropicalis* is disclosed in U.S. Pat. No. 4,474,882. The unsaturated dicarboxylic acids correspond to the starting materials in the number and position of the double bonds. Similar processes in which other special microorganisms are used are described in U.S. Pat. Nos. 3,975,234 and 4,339,536, in British Patent Specification 1,405,026 and in German Patent Publications 21 64 626, 28 53 847, 29 37 292, 29 51 177, and 21 40 133.

In a copending application, Ser. No. 07/432,091, filed Nov. 11, 1989, now U.S. Pat. No. 5,254,466, a method of producing alpha, omega-dicarboxylic acids in high yields by culturing *C. tropicalis* strains having disrupted chromosomal POX4A, POX4B and both POX5 genes is disclosed. The POX4 and POX5 gene disruptions effectively block the B-oxidation pathway at its first reaction (which is catalyzed by acyl-CoA oxidase) in a *C. tropicalis* host strain. The POX4 and POX5 genes encode distinct subunits of long chain acyl-CoA oxidase, which are the peroxisomal polypeptides (PXPs) designated PXP-4 and PXP-5, respectively. The disruption of these genes results in a complete block of the β-oxidation pathway thus allowing enhanced yields of dicarboxylic acid by redirecting the substrate toward the omega-oxidation pathway and also prevents reutilization of the dicarboxylic acid products through the β-oxidation pathway.

The specific productivity (grams of dicarboxylic acid/liter/hr) of substantially pure alpha, omega-dicarboxylic acids should be increased by culturing a *C. tropicalis* strain in which the chromosomal POX4A, POX4B and both POX5 genes have been disrupted and which also has a greater number of P450 genes than the wild type. The substrate flow in such a strain would be redirected to the omega-oxidation pathway as the result of functional inactivation of the competing β-oxidation pathway by POX gene disruption, while an increase in the amount of rate-limiting omega-hydroxylase through P450 gene amplification should increase the rate of substrate flow through the omega-oxidation pathway.

SUMMARY OF THE INVENTION

One aspect of the present invention provides a process for increasing the omega-hydroxylase activity in *C. tropicalis* comprising amplifying one or more P450 genes in said *C. tropicalis*.

Another aspect of the present invention provides a transformed *C. tropicalis* host having a greater number of P450 genes than the wild type.

Still another aspect of the present invention provides a transformed *C. tropicalis* host having a greater number of P450 genes than the wild type wherein up to four chromosomal POX4 and POX5 genes are disrupted.

Yet another aspect of the present invention provides a process for increasing the specific productivity of substantially pure alpha, omega-dicarboxylic acids in substantially quantitative yield comprising culturing an amplified *C. tropicalis* strain in a culture medium containing a nitrogen source, an organic substrate and a cosubstrate.

BRIEF DESCRIPTION OF THE DRAWINGS

FIG. 1 is a schematic representation of plasmid vectors used for amplification of the P450ALK and P450RED genes in *C. tropicalis*. Plasmid pCU3ALK1 contains the P450ALK gene subcloned on a 4.4 Kb DNA fragment into the Eco R1 site of pCU3. Plasmid pCU3ALK2 contains the same DNA fragment subcloned in the opposite orientation. Plasmid pCU3RED contains the P450RED gene subcloned on a 3.7 Kb DNA fragment into the Eco R1 site of pCU3.

FIG. 3 is a description of P450-amplified strains obtained by transformation of *C. tropicalis* SU-2 (ATCC 20913) with either the P450ALK or P450RED genes.

FIG. 4 is a description of some P450-amplified strains obtained by transformation of strain H5343 (ATCC 20962) with either the P450ALK or P450RED genes or both by cotransformation.

DESCRIPTION OF THE PREFERRED EMBODIMENTS

Figure 2:
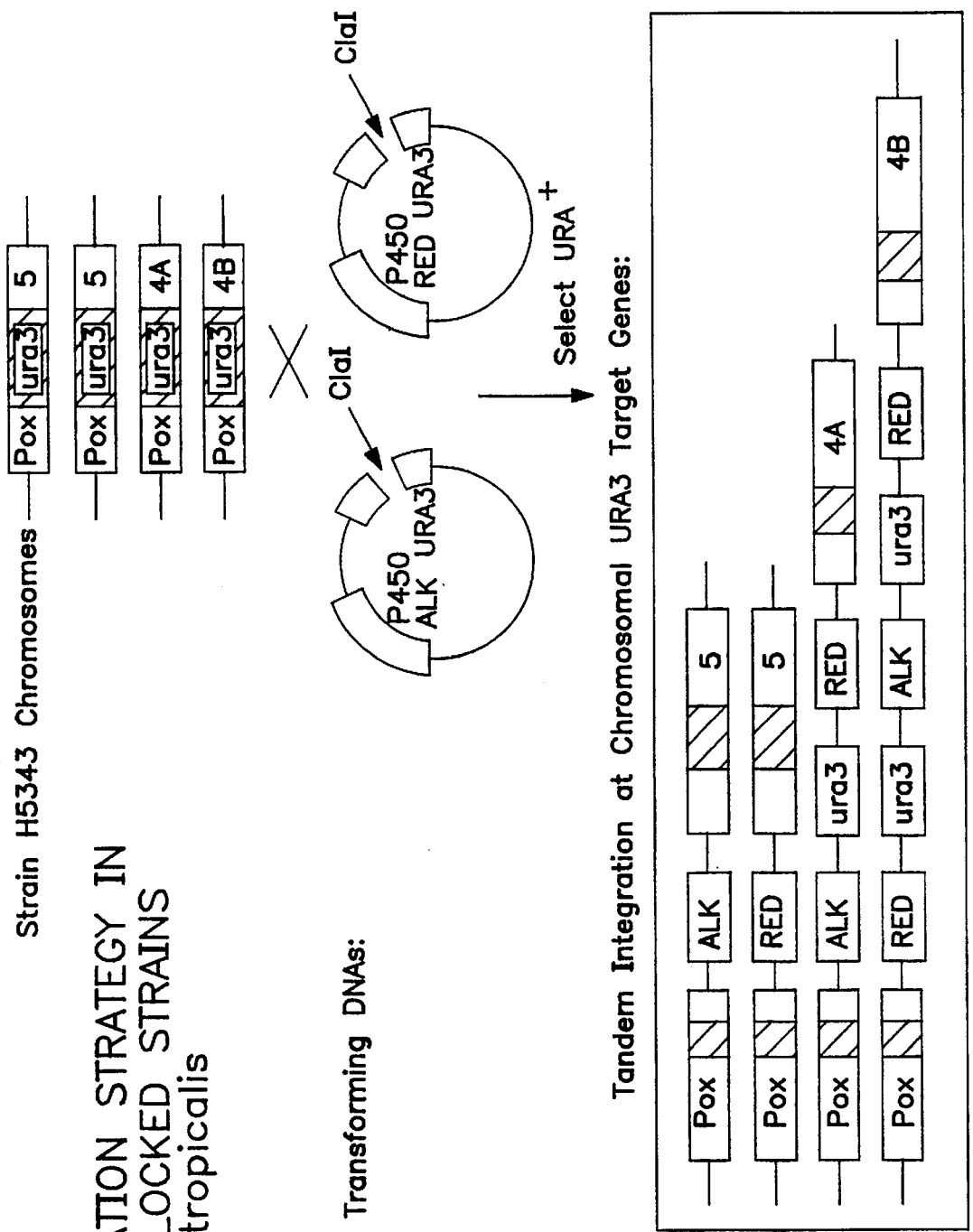
FIG. 2 is a schematic representation of the strategy used to amplify both P450 genes in the beta-oxidation blocked strain H5343 (ATCC 20962).
Figure 5:
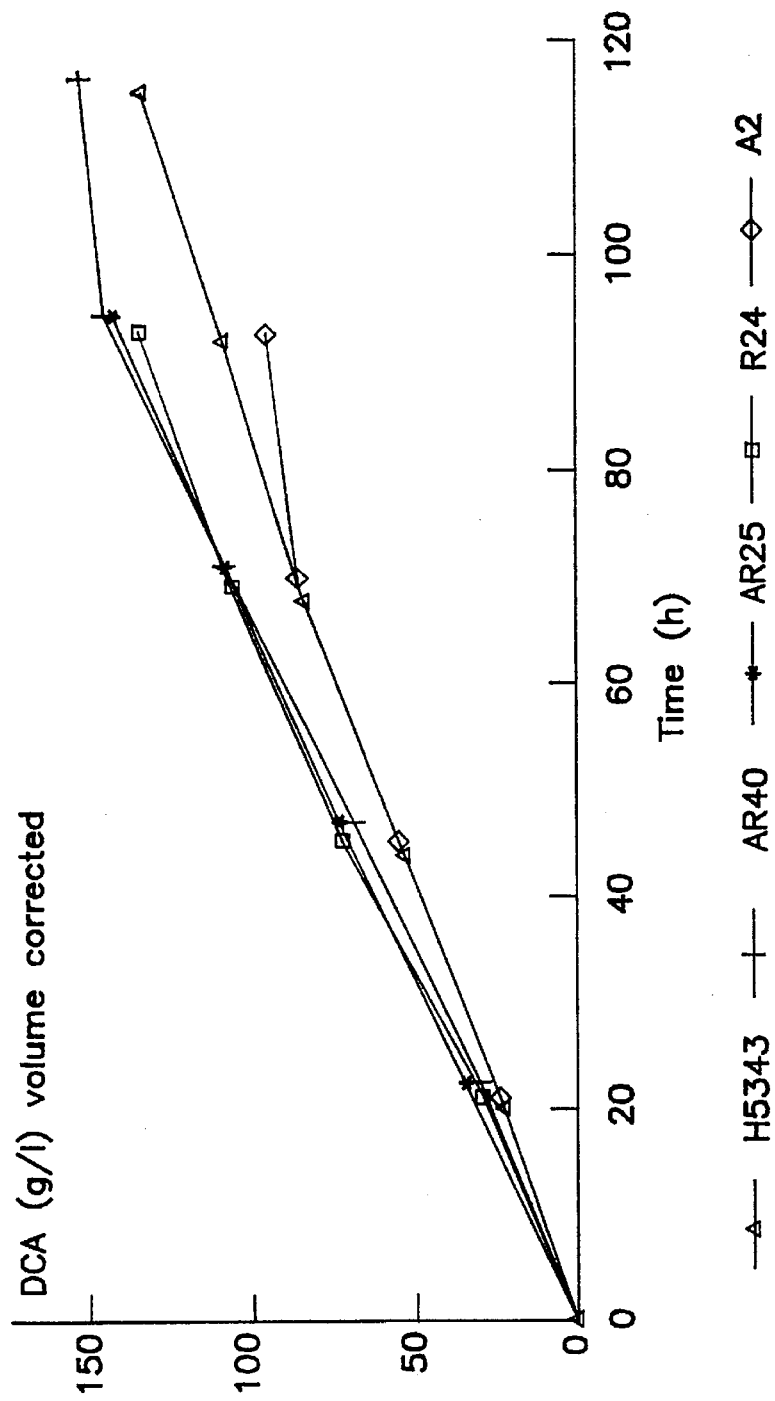
FIG. 5 is a graphical comparison of the dicarboxylic acid (DCA) production of the various P450-amplified strains derived from strain H5343.

One aspect of the present invention provides a process for increasing the omega-hydroxylase activity in *C. tropicalis* comprising amplifying one or more P450 genes in said *C. tropicalis*. Amplifying one or more P450 genes means increasing the copy number of one or more P450 genes. The copy number of the P450 gene or genes can be increased by transforming a *C. tropicalis* host with any type of vector which will introduce one or more P450 genes into the *C. tropicalis* host cell. A vector is defined as any linear or circular DNA molecule capable of introducing a fragment of foreign DNA into a host cell. A P450 gene is defined as a cytochrome P450ALK1, P450ALK2, P450RED, or a combination of P450ALK and P450RED genes. A P450ALK1 gene is a cytochrome P450 gene. A P450ALK2 gene is a cytochrome P450 gene in opposite orientation with respect to the DNA sequence having homology to a target site in the genome (See FIG. 1). The vector can be either an integrating vector or a non-integrating vector. An integrating vector is one which has a DNA sequence with homology to a target site in the genome of the host cell so that vector DNA can be integrated into the nuclear DNA of the host *C. tropicalis*. Integrating vectors, known to those skilled in the art as YIp vectors, are composed of a bacterial cloning vector carrying a suitable yeast gene which can be used in the selection of suitable yeast transformants and which provides homology to promote integration of the vector DNA into the nuclear DNA of recipient yeast cell. The vector can also be an non-integrating vector in that it may not be integrated into the nuclear DNA of the host *C. tropicalis*. A P450RED gene is a NADPH-cytochrome P450 reductase gene. The term combination of P450ALK and P450RED genes means that both genes have been used to transform a *C. tropicalis* host cell and have been integrated into the genome of the transformed host cell in any relative amount and in any order of introduction.

The integrating vector will also have a DNA sequence which has homology to a target site in the genome of the host cell so that vector DNA can be integrated into the nuclear DNA of the host *C. tropicalis*. Preferably, the DNA sequence contained in the vector will be a selectable marker gene, a non-functional copy (or copies) of which is (are) also present in the nuclear DNA of *C. tropicalis* such as a URA3A, URA3B, or HIS4 genes. In a case where the host's genome has all of its POX4 and POX5 genes inactivated, for example, as the result of multiple gene disruptions, as is the case with strain H5343, the selectable marker contained in the vector can be a POX4 or POX5 gene. The fact that the DNA sequence in the vector has homology to some portion of the host's genome makes it integratable into the genome in the region of homology. The term integratable means capable of being inserted into a host genome as a region covalently linked on either side to the host sequences. The region of the host genome into which the DNA sequence from the vector is integrated is defined as the target site.

The term tandem integration is understood to mean the creation of an additional target site or sequence in the host cell genome as a result of integration of the DNA sequence from the vector. The tandem integration process is illustrated in FIG. 2.

While the process of the present invention is especially suitable for use with strains in which the β-oxidation pathway is completely blocked, such as strain *C. tropicalis* H5343 (ATCC 20962) wherein all four POX4 and POX5 genes are disrupted, it can be used with a wild-type strain or with strains in which the β-oxidation pathway is partially blocked. The following strains can be transformed with one or more integration vectors comprised of a URA3 selectable marker and P450ALK and P450RED genes. These are strains designated as H41 in which the POX4A gene is disrupted, H41B in which the POX4B gene is disrupted, H43 in which the POX4A and POX4B genes are disrupted, H51 in which one POX5 gene is disrupted, H53 in which both POX5 genes are disrupted, H45 in which one POX5 and the POX4A genes are disrupted, strain H534 in which both copies of POX5 and the POX4A gene are disrupted, H534B in which both copies of POX5 and the POX4B gene are disrupted, and H435 in which one of the POX5 and the POX4A and POX4B genes are disrupted.

The transformed strains will have amplified P450ALK and P450RED genes relative to the untransformed strains and will demonstrate higher specific omega-hydroxylase activity than the untransformed strains following induction with the appropriate substrates.

In one embodiment of the present invention, transformation of strain *C. tropicalis* SU-2 (ATCC 20913) by integration of a P450-URA3 vector into the native ura3 gene of the SU-2 genome results in the presence of two URA3 genes. Multiple tandem integration is also possible since more than one P450-URA3 vectors can be integrated at the same time. Integration of a P450 vector results in an increased gene copy number of the P450 gene in the host genome by tandem integration or multiple tandem integration.

In a preferred embodiment, strain H534 is transformed with one or more integration vectors comprised of a URA3 selectable marker and P450ALK and P450RED. The transformed *C. tropicalis* strains are amplified for the P450ALK and P450RED genes relative to *C. tropicalis* H534. Biochemical analysis has shown these transformants to demonstrate higher specific omega-hydroxylase activity than H534 following induction with the appropriate substrates.

In another preferred embodiment, strain H435 is transformed with one or more integration vectors comprised of a URA3 selectable marker and P450ALK and P450RED. The transformed *C. tropicalis* strains are amplified for the P450ALK and P450RED genes relative to *C. tropicalis* H435, based on DNA/DNA hybridization analyses.

In a particularly preferred embodiment, *C. tropicalis* H5343 (ATCC 20962), wherein all four POX4 and POX5 genes are disrupted by a URA3 selectable marker, is transformed with one or more integration vectors comprised of a URA3 selectable marker and either a P450ALK gene or a P450RED gene through multiple tandem integrations. The transformed *C. tropicalis* strain, AR40, contains an estimated three-fold amplification of the P450ALK gene and a two-fold amplification of the P450RED gene relative to *C. tropicalis* H5343 as determined by the general method described in Example 5. Culturing AR40 cells in a culture medium containing a nitrogen source, an organic substrate (methyl myristate) and a cosubstrate (glucose) for 100 hours results in an approximately 17% increase in the specific production (g/L/hr) of substantially pure tetradecanedioic acid relative to strain H5343 (150 g/L/95 hrs compared to 128 g/L/95 hrs). Since the transformed cells have all four POX4 and POX5 genes disrupted there is no production of acyl-CoA oxidase, an enzyme required in the initial step of the beta-oxidation pathway. The elevated copy number of the P450ALK and P450RED genes results in an increase in omega-hydroxylase level which catalyzes the first step in omega-oxidation. The substrate is directed toward the omega-oxidation pathway while preventing both substrate degradation and reutilization of the dicarboxylic acid products through the β-oxidation pathway. The determination of the increase in the omega-hydroxylase activity in the transformed *C. tropicalis* H5343 is described in Example 4. The results are reported in FIG. 4 as % lauric acid conversion normalized to the microsome protein concentration.

Another aspect of the present invention provides a a transformed *C. tropicalis* host having a greater number of P450 genes than the wild type. Such a strain is defined as an amplified strain because one or more of the P450 genes have been amplified. The degree of amplification is a measure of the extent to which the copy number of a P450 gene or genes has been increased. The greater the increase in the copy number, the greater is the increase in the degree of amplification. FIG. 3 is a description of P450-amplified strains obtained by transformation of *C. tropicalis* SU-2 (ATCC 20913) with either the P450ALK or P450RED genes. FIG. 4 is a description of P450-amplified strains obtained by transformation of strain H5343 (ATCC 20962) with either the P450ALK or P450RED genes or both by cotransformation. Strain H5343 has all four chromosomal POX genes—POX4A POX4B, and both POX5 genes—disrupted.

Yet another aspect of the present invention provides a process for increasing the specific productivity of pure alpha, omega-dicarboxylic acids in substantially quantitative yield by *C. tropicalis* comprising culturing a transformed *C. tropicalis* host having a greater number of P450 genes than the wild type and wherein up to all four chromosomal POX4 and POX5 genes are disrupted in a culture medium containing a nitrogen source, an organic substrate and a cosubstrate. The specific productivity is the amount of dicarboxylic acid produced per liter of culture broth per hour and is expressed in grams/liter/hour. The culture medium can contain any inorganic or organic source of nitrogen normally used in processes for culturing microorganisms. Inorganic nitrogen sources include alkali metal nitrates such sodium or potassium nitrate, ammonium salts such as ammonium sulfate, ammonium chloride, ammonium nitrate, ammonium acetate, etc. Organic nitrogen sources include urea, corn steep liquor, yeast extracts, and other organic nitrogen sources known to those skilled in the art. The organic substrate can be any aliphatic compound wherein at least one of the terminal carbons is a methyl group and which has from about 4 to about 22 carbon atoms. Such compounds include alkanes, alkenes, alkynes, carboxylic acids and their esters, and arenes. Preferred substrates are alkanes having from about 4 to about 22 carbon atoms and fatty acids and their methyl or ethyl esters wherein the acyl portion contains from about 4 to about 22 carbon atoms. The most preferred substrates are dodecane, tridecane, tetradecane, oleic acid, methyl oleate, methyl palmitate, methyl palmitoleate and methyl myristate.

The cosubstrate is selected from the group consisting of glucose, fructose, maltose, glycerol and sodium acetate. The preferred cosubstrate is glucose. A cosubstrate is necessary because the beta-oxidation pathway of *C. tropicalis* H5343 is totally blocked, and energy is not available from the oxidation of the substrate. Glucose added at a definite rate along with the substrate strikes a balance between providing an energy source for the cells while allowing the partial oxidation of the substrate to an alpha, omega-dicarboxylic acid.

In a preferred embodiment, a fermentation medium comprising 3 g/l peptone, 6 g/l yeast extract, 6.7 g/l Yeast Nitrogen Base (Difco), 3 g/l sodium acetate, 7.2 g/l potassium phosphate, dibasic (trihydrate), 9.3 g/l potassium phosphate, monobasic, and 75 g/l glucose is prepared and sterilized by heating to 121° C. at 15psi. The medium is then inoculated with a 10% (v/v) inoculum of a preculture grown on the same medium. Strain AR40 is then grown at 30° C. for a time sufficient to produce a maximum cell density. The maximum cell density is determined by measuring the turbidity of the medium as indicated by an absorbance reading of from about 60 to about 70 at a wavelength of 625 nm. The maximum cell density corresponds to a viable cell count of about $1.5 \times 10^9$ per ml.

After achieving the maximum cell density, the pH of the medium is then raised from pH 6.5 to a value from about 7.5 to about 9.5 with preferred value being in the 7.8 to 8.9 range. The cosubstrate is added at a rate from about 0.5 to about 2.5 grams per hour per liter of fermentation broth. The preferred rate of addition of glucose is from about 1.5 to about 1.75 grams per hour per liter of fermentation broth. The substrate is added simultaneously with the cosubstrate (glucose) at such a rate as to maintain the substrate concentration of from about 4 to about 40 grams per liter of fermentation broth. The preferred rate of addition of substrate is from about 10 to about 20 grams per liter of fermentation broth. The fermentation can be continued as described above indefinitely in the case of a continuous process or until the working volume of the fermentation vessel is reached in the case of a batch process.

The following examples are meant to illustrate but not limit the invention.

EXAMPLE 1

Construction of pCU3

Plasmid pCU3 was constructed by subcloning a 2.2 Kb NruI/SacI restriction fragment containing the entire URA3 gene from plasmid pCU2dSacI into the HincII/SacI polylinker cloning site of pUC19. Plasmid pCU2dSacI contains the entire *C. tropicalis* URA3A gene on a 2.8 Kb EcoR1/SacI restriction fragment.

EXAMPLE 2

Preparation of Amplification Vectors pCU3ALK1 and pCU3ALK2

The P450ALK gene was first subcloned on a 4.1Kb BamHI fragment from pDS-1 (a plasmid containing the *C. tropicalis* ATCC#750 P450ALK gene which was obtained from J. Loper, University of Cincinatti; Gene 76; 121–136 (1989)) into the BamHI site of pBR322. For this construction, 5 ug pDS-1 was digested with the BamHI restriction endonuclease and was ligated to 3 ug of BamHI linearized, dephosphorylated pBR322. The ligation mixture was used to transform *Escherichia coli* DH5a (BRL, Bethesda, Md.) to ampicillin resistance. Restriction analysis of 20 independent ampicillin resistant, tetracycline sensitive isolates showed two of them to contain the expected construction. These plasmids are designated as pTR1. The P450ALK fragment from pTR1 was subcloned on a 4.4 Kb HindIII fragment into the pCU3 vector containing the URA3A selectable marker. For this construction, 25 ug of pTR1 was first treated with EcoR1 methylase (20 Units) (New England Biolabs, Beverly, Mass.) and digested to completion with HindIII (20 Units). Following filling-in of the cohesive ends with DNA polymerase Klenow fragment and the addition of EcoR1 linkers using standard techniques (Maniatis et al., Molecular Cloning: A Laboratory Manual, Cold Spring Harbor, 1982), the DNA was ligated to 0.2 ug EcoR1 linearized and dephosphorylated pCU3. The ligation mixture was used to transform *E.coli* DH5a (BRL, Bethesda, Md.) to ampicillin resistance. Restriction analysis of the plasmid DNA from 24 transformants showed three to contain the expected construction. Two of these are in the same orientation as the URA3A gene and are designated pCU3ALK1 while one is in opposite orientation and designated pCU3ALK2.

EXAMPLE 3

Preparation of Amplification Vector pCU3RED

The P450RED gene was subcloned on a 3.7 Kb SpeI fragment from pTS1 (a plasmid containing the *C. tropicalis* ATCC#750 P450RED gene which was obtained from J. Loper, University of Cincinatti) into the pCU3 vector. For this construction, 25 ug of pTS1 was first treated with EcoR1 methylase (20 Units)(New England Biolabs, Beverly, Mass.) and digested to completion with SpeI (16 Units). Following filling-in of the cohesive ends with DNA polymerase Klenow fragment and the addition of EcoR1 linkers using standard techniques (Maniatis et al., Molecular Cloning: A Laboratory Manual, Cold Spring Harbor, 1982), the DNA was ligated to 0.2 ug EcoR1 linearized and dephosphorylated pCU3. The ligation mixture was used to transform *E.coli* DH5a (BRL, Bethesda, Md.) to ampicillin resistance. Restriction analysis of the plasmid DNA from 24 ampicillin resistant transformants showed one to contain the expected construction, designated pCU3RED.

EXAMPLE 4

General Transformation Procedure

A colony of *C. tropicalis* was inoculated into about 10 ml YEPD medium and the culture shaken at 30° C. overnight. Cells were diluted to an absorbance at 600 nm ($A_{600}$) equal to about 0.01–0.1 and were maintained in log growth phase in YEPD medium at 30° C. Then 0.03 ml of the culture diluted to an $A_{600}$ 0.01 was inoculated into 100 ml YEPD medium and the culture was shaken at 30° C. overnight. After harvesting the culture at $A_{600}$ 0.2–0.3 by centrifugation at 1500×g for 5 min, the cells were washed once with 10 ml sterile water, once with 10 ml freshly prepared SED (SED=1M sorbitol, 25 mM EDTA, 50 mM DTT, filter sterilized), once with 10 ml 1M sorbitol and then resuspended in 5 ml SCE buffer (SCE=1.0M sorbitol, 100 mM sodium citrate, pH 5.8, 10 mM EDTA). Zymolyase 20000 (20 µl of 4 mg/ml) was then added and the mixture was incubated at 30° C. Spheroplast formation was monitored as follows: 100 µl aliquots of cells were added to either 900 µl of 0.2% SDS or 900 µl of 1M sorbitol. The incubation with the Zymolyase was terminated at the point at which cells lysed in SDS, but not in sorbitol (usually 15–30 min of incubation). Spheroplast formation was efficient, with an estimated 99% of the cells becoming osmotically fragile. At the termination of the incubation, the spheroplasts were washed once with 10 ml 1M sorbitol by centrifugation at 1,000×g for 10 min, once with 10 ml of sterile CaS (CaS=1M sorbitol, 10 mM calcium chloride, filter sterilized) and then resuspended in a total of 0.6 ml of CaS. Transformation was achieved by adding DNA samples (5–10 ug/20 µl ) to 12×75 mm sterile polypropylene tubes; the DNA was in water or TE buffer. 100 µl of spheroplast was added to the DNA sample and the mixture incubated at room temperature for 20 min. 1 ml of PEG solution (PEG solution=20% polyethylene glycol—3350, 10 mM calcium chloride, 10 mM Tris.HCl, pH 7.4, filter sterilized) was then added to the mixture and incubated at room temperature for 15 min. After centrifuging the samples at 1,000×g for 10 min, the PEG solution was decanted, and the samples were resuspended in 150 µl of SOS (SOS=1M sorbitol, 30% YEPD medium, 10 mM calcium chloride, filter sterilized) and then incubated for 30 min at room temperature. To the sample was then added 850 ml of sterile 1M sorbitol. For regeneration of cells, 10 µl and 990 µl aliquots of each sample were added to 10 ml aliquots of melted regeneration agar held at 50° C. and the mixture poured onto plates containing a solid 10 ml bottom agar layer of regeneration agar. Regeneration agar was prepared by autoclaving 9 g of bacto-agar and 13.5 g KCl in 240 ml of water; after autoclaving, 30 ml of 20% sterile dextrose and 30 ml of sterile 10× YNB was added and the mixture held at 55° C. Ten ml of bottom layer agar was poured onto plates 30 minutes before the transformation samples were ready. Regeneration of protoplasts was efficient and was greater than 10%. Transformation of ura3 strains of *C. tropicalis,* for example strain SU-2, occurred at a high frequency. The frequency of transformation was about 5,000–20,000 $Ura^+$ colonies per microgram of DNA. Both closed circular and linear plasmid DNAs gave a high frequency of transformation. The efficiency was about 10- to 100-fold less using the LiCl transformation method. For transformation of *C. tropicalis,* the URA3A selectable marker contained on the plasmids containing the P450 genes provides the homology to direct the integration to the analogous site(s) within the yeast genome. Since the DNA sequence at the ends of a linear DNA fragment dictate the exact site of integration into the yeast genome, digestion of any of these plasmids with the ClaI restriction endonuclease is suitable for targeting their integration to the chromosomal *C. tropicalis* ura3A locus. Therefore, the pCU3ALK1, pCU3ALK2 and pCU3RED plasmids were linearized by digestion with the ClaI restriction endonuclease and transformed, separately or in combination, into the appropriate *C. tropicalis* strains by selection for the Ura+ phenotype. In particular, for transformation of strains in which URA3 selectable marker was previously used for the disruption of the chromosomal POX4 or POX5 genes, the uracil requirement of these strains was first restored by selecting for spontaneous mutations within the URA3 selectable marker.

EXAMPLE 5

Determination of Omega-Hydroxylase Activity

About 0.05 mg of microsomes were incubated in the presence of 4.5mM NADPH$_2$ and $^{14}$C-labelled lauric acid (2.5×10$^5$ cpm; 100 uCi/ml diluted about 1:300) in 255 ul 0.1M Tris pH 7.5 for 30 minutes at 30° C. The reaction was stopped with the addition of 100 ul 6N HCl. Following extraction and subsequent concentration with diethyl ether, the labelled products were separated on a silica gel 60 TLC plate, and run in toluene:acetic acid (10:1) until saturation. The lauric acid and 12-hydroxy-lauric acid reaction product were identified by their relative mobilities upon autoradiography and were quantitated in a scintillation counter following excision of the appropriate radioactive spots. The results are reported in FIG. 3 and FIG. 4 as % lauric acid conversion normalized to the microsome protein concentration.

EXAMPLE 6

Determination of NADPH Reductase Activity

NADPH-reductase activity was determined kinetically by following the reduction of cytochrome c at 550 nm (Beaufay et al., (1974) Journal of Cell Biology 61; 188–200). Microsomes were diluted and added to a reaction mixture consisting of 40 mM KPO$_4$, 32 mM nicotinamide, 50 uM cytochrome c and 0.25 mM sodium cyanide. The reaction was initiated with the addition of 0.1 ml of 2.25 mM NADPH$_2$. The results are reported in FIG. 3 and FIG. 4 as the change in $A_{550}$/min/mg.

EXAMPLE 7

General Procedure for Identifying Strains Containing Single or Multiple Integrations of P450 Genes Genomic DNA's from Ura+ transformants were isolated, digested with SalI and analyzed by Southern hybridization to P450ALK, P450RED and URA3A probes. Since there are no internal SalI sites within either plasmid, the fragment sizes generated by SalI digestion depend solely upon the location of the SalI sites nearest the site of chromosomal integration. Thus, tandem integration into the genome results in a single large fragment, the size of which is directly proportional to the number of tandem integrations. Transformants containing single, double or multiple tandem integrations of either the P450ALK or P450RED genes or both genes were identified. As expected, all ClaI linearized plasmids were integrated intact at the *C. tropicalis* ura3A locus.

EXAMPLE 8

Identification of Strain AR40

The results of biochemical analysis demonstrated that the P450 genes are functionally expressed in *C. tropicalis* and that the overall omega-hydroxylase activity was increased in response to the number of P450 genes integrated into the yeast genome. In comparison to the wild-type, SU-2, integration of a single cytochrome P450 gene resulted in a 1.5-fold increase in the omega-hydroxylase specific activity, regardless of the orientation of the P450ALK gene in the chromosome (strains SA1C1 and SA2C1a). This suggests that the gene is expressed from its own regulatory elements and not from flanking chromosomal DNA. Integration of additional P450ALK genes (strains SA1C2, SA1CM, SA2CM) did not result in any further increase. Integration of a single P450RED gene into the yeast genome (strain SRC1) resulted in a 1.5-fold enhancement of omega-hydroxylase activity while multiple copies (SRCM) resulted in 2.8-fold activity increase. Transformants containing one or more P450RED genes (SRC1 and SRCM) showed 3-fold and 7-fold higher specific NADPHreductase activity than the wild-type, respectively. Since the P450 amplification in the wild-type strain established the feasibility of this approach, both P450 genes were subsequently amplified in the strains containing partial or complete blockage of the B-oxidation pathway. Accordingly, the P450ALK and P450RED genes were transformed, separately and in combination, into uracil requiring derivatives of strains H5343, H543 and H435. The integrations were targeted to the multiple chromosomal ura3 loci, present in these strains as the result of previous gene disruptions making use of the URA3A selectable marker to disrupt the chromosomal POX4 and POX5 genes. While most co-transformations resulted in multiple tandem integrations, the exact number of integrations could not be accurately resolved with conventional electrophoresis due to the extreme size of the integration. The site of integration was determined by hybridization to POX gene probes, again based on the increase in the size of the target gene. These studies have shown that most strains contain multiple P450 integrations into both disrupted POX4 genes and one of the disrupted POX5 genes. Biochemical analysis of representative strains by assay for omega-hydroxylase and NADPH reductase activities showed a correlation between the number of P450 genes integrated into the Candida genome and the overall omega-hydroxylase activity. Again, these results show the importance of amplifying the reductase component of the hydroxylase complex. A greater increase in the overall hydroxylase activity was achieved by amplification of the reductase gene (P450RED) relative to the monooxygenase gene (P450ALK). However, since both proteins must function together in the microsomal membrane, the largest overall increase in activity was achieved by simultaneous amplification of both genes in the same strain. Strain AR40, which demonstrated 1.9 fold higher omega-hydroxylase activity than the B-oxidation blocked parental strain (H5343), was identified. Since the biochemical analyses described above have shown these strains to possess increased hydroxylase activity, they should be capable of converting fatty acid methyl ester substrates to diacid products faster than strain H5343. To test this, H5343 and representative P450-amplified strains, containing one or both P450 genes amplified to various degrees, were separately cultured in duplicate in 100 ml of medium containing 0.67% YNB, 0.01M KPO4 pH 7.8, 0.5% yeast extract, 0.5% peptone, 2% glycerol and 2% methyl oleate (99% pure). The cultures were incubated at 30° C. and sampled at 24 hr, 36 hr and 48 hr for GC analysis to quantitate substrate and product levels. The P450-amplified strains demonstrated significantly higher productivity than H5343. Most notable in these comparisons to H5343 (0.7 g/l /36hr or 11.1g/l/48 hr) were strains AR40 (11.9 g/l/36 hr), AR25 (12.7 g/l/36 hr), Co5 (16.3 g/l/48hr) and Co34 (16.0 g/l/48 hr). No products other than octadecanedioic acid and diacid derivatives of contaminants present in the substrate were identified by GC, attesting to the specificity of these conversions.

EXAMPLE 9

Standard Fermentation Procedure

The fermentor medium consisted of (per liter): peptone, 3 g; yeast extract, 6 g; yeast nitrogen base, 6.7 g; sodium acetate, 3 g; potassium phosphate dibasic trihydrate, 7.2 g; potassium phosphate monobasic, 9.3 g. Glucose was sterilized separately and was added to the medium to a final concentration of 75 g/l. The final pH of the medium was 6.5.

Individual strains were first precultured in a shake flask using the fermentation medium described above. The flask was inoculated with a 0.4% inoculum of a frozen glycerol stock. After inoculation, the flask was incubated at 30° C. and 250 RPM until the culture reached early stationary phase (approximately 24 h). The preculture was used to inoculate (a 10% inoculum was used) a fermenter containing the same medium. The culture was grown at 30° C. and 1300 rmp until a maximum turbidity was reached. This was determined by measuring the optical density at 625 nm. The aeration rate was 1 vvm.

Following this initial growth period, the transformation phase was started by the addition of substrate at a rate sufficient to accumulate between 10 and 20 g/l within the first 24 h. Thereafter the dosing rate was altered to maintain a desired concentration between 5 and 30 g/l. A cosubstrate, glucose, was dosed concurrently with the substrate at a rate sufficient to maximize productivity, generally between 1.1 and 1.6 g/l/h. For the amplified strains, using the medium described, a glucose dosing rate of 1.6 g/l/h was found to be optimal. At the start of the transformation phase the pH was also raised to between pH 7.8 and 8.9. The lowest pH which maintains the solubility of the product is selected, since at higher pH values, more base is required to maintain the pH, due to the formation of carbonate, a by-product of the metabolism of the cells. The pH could be raised as necessary to maintain the solubility of the dicarboxylic acid formed in the process. The aeration rate was adjusted to maintain an oxygen saturation level of 80%. During the transformation phase, below 50% saturation allows formation of incomplete oxidation products, namely omega-hydroxylated by-products.

Samples were periodically removed and analyzed for concentration of substrate and product; 1 ml of sample was acidified with 0.4 ml of 6N HCl and extracted into t-butylmethyl ether. The analyses were performed gas chromatographically after silation of the free acids.

Methylmyristate was used as substrate for the comparison of the productivity of the various amplified strains. Tetradecanedioic acid was the product. During the transformation phase, glucose was dosed at a concentration of 1.6 g/l/h for the amplified strains and 1.1 g/l for strain H5343. At the start of the transformation phase the pH was raised to 8.3+/–0.1. After 24 to 36 h the pH was again raised to 8.8+/–0.1. The efficiency of transformation of substrate into product was normally greater than 90%, and the purity of the product was dependent on the purity of the substrate.

EXAMPLE 10

Specific Productivity of Various Amplified Strains

The specific productivity of five strains were chosen on the basis of the type and degree of amplification. Strain H5343 (ATCC 20962), the non-amplified strain, was the control strain. Strain A2 had approximately 1 additional cytochrome P-450 gene amplified. Strain R24 had multiple copies of the reductase gene. Strains AR25 and AR40 had both genes amplified; AR25 was estimated to have 2 additional copies of both genes, while strain AR40 had 3 copies of the cytochrome gene and 2 copies of the reductase gene (FIG. 4). FIG. 2 shows the results of the comparison of these five strains. The strains containing amplified P450 genes demonstrated productivities 25–30% higher than the non-amplified strain, H5343.

EXAMPLE 11

Construction of a POX5 Disruption Cassette

In preparation for the disruption of the C. tropicalis chromosomal POX5 genes, the URA3A selectable marker was subcloned into the isolated POX5 gene contained on plasmid pKD1dBamHI (see Example 26). The POX5 gene has been previously cloned and its DNA sequence determined (Okasaki, K., et al., (1988) PNAS, USA 83; 1232–1236). For the development of a POX5 disruption vector, 12 ug of plasmid pCU2dSacI (see Example 25) containing the C. tropicalis URA3A gene was linearized by digestion with the NruI restriction endonuclease. BamHI linkers were ligated to these DNA fragments by standard procedures (Maniatis et al., Molecular Cloning: A Laboratory Manual, Cold Spring Harbor, 1982) and following digestion with the BamHI restriction endonuclease, the URA3A gene was liberated on a 2.2 Kb BamHI restriction fragment. The URA3A gene was then ligated to 1.25 ug of BamHI linearized, dephosphorylated pKD1dBamHI plasmid (see Example 26). This plasmid contains the C. tropicalis POX5 gene cloned on a 3.9 Kb EcoR1 restriction fragment into the unique EcoR1 site of pBR322. To facilitate the URA3A subcloning into the unique POX5 BamHI site, the BamHI site within the tetracycline resistance gene of pBR322 was previously destroyed by filling-in with Klenow polymerase following partial BamHI digestion. The ligation mixture was used to transform E. coli DH5alpha (BRL, Bethesda Md., USA) to ampicillin resistance. Restriction analysis of plasmid DNA from 95 ampicillin resistant transformants showed one to contain the expected construction. This plasmid, designated pKD1-URA3A, contains the URA3A gene cloned on a 2.2 Kb BamHI fragment into the unique POX5 BamHI restriction site (position #1178) and is flanked by 1.2 Kb of 5'-POX5 sequence and 2.7 Kb of 3'-POX5 sequence. Digestion of the plasmid with the EcoR1 restriction endonuclease liberates the 5'-pox5-URA3A-pox5-3' cassette suitable for disruption of the C. tropicalis chromosomal POX5 gene.

EXAMPLE 12

Construction of a POX4 Disruption Cassette

In preparation for the disruption of the chromosomal POX4 genes, the URA3A selectable marker was first subcloned into the isolated POX4 gene contained on plasmid pKD3dBamHI (see Example 27). The POX4 gene has been previously cloned and its DNA sequence determined (Okasaki, K., et al., 1986, PNAS, USA 83; 1232–1236). For the development of a POX4 disruption vector, 12 ug of plasmid pCU2dSacI (see Example 25) was linearized by digestion with the NruI restriction endonuclease. BamHI linkers were ligated to these DNA fragments by standard procedures (Maniatis et al., Molecular Cloning: A Laboratory Manual, Cold Spring Harbor, 1982) and following digestion with BamHI restriction endonuclease, the URA3A gene was liberated on a 2.2 Kb BamHI restriction fragment. The URA3A gene was then ligated to 0.75 ug of BamHI linearized, dephosphorylated pKD3dBamHI plasmid. This plasmid contains the POX4 gene cloned on a 6.6 Kb HindIII fragment into the unique HindIII restriction site of pBR322. To facilitate the URA3A subcloning into the unique BamHI site of the POX4 gene, the BamHI restriction site within the tetracycline resistance gene of pBR322 was previously destroyed by filling-in with Klenow polymerase following partial BamHI digestion. The ligation mixture was used to transform E. coli DH5alpha (BRL, Bethesda, Md., USA) to ampicillin resistance. Restriction analysis of plasmid DNA from 92 transformants showed one to contain the expected construction. This plasmid, designated pKD3-URA3A, contains the URA3A gene cloned on a 2.2 Kb BamHI fragment into the unique POX4 BamHI site (pos#2101) and is flanked by 2.1 Kb of 5'-POX4 sequence and 4.5 Kb of 3'-POX4 sequence. Digestion of this plasmid with the EcoR1 restriction endonuclease liberates the 5'-pox4-URA3-pox4-3' cassette suitable for disruption of the C. tropicalis chromosomal POX4 gene.

EXAMPLE 13

Disruption of the C. tropicalis Chromosomal POX5 Gene

C. tropicalis strain SU-2 (ATCC 20913) spheroplasts were transformed to uracil prototrophy with EcoR1 digested pKD1-URA3A as described in Example 4.

Following transformation with 5 ug EcoR1 digested pKD1-URA3A, approximately 200 mitotically stable Ura+ transformants were recovered. Eleven transformants were subsequently screened for growth on dodecane and by Southern hybridization of EcoR1 digested genomic DNA to POX5 and URA3A probes by standard methods (Maniatis et al., Molecular Cloning: A laboratory Manual, Cold Spring Harbor, 1982). All eleven transformants demonstrated growth on dodecane comparable to the wild-type. Hybridization of EcoR1 digested genomic DNA from these transformants to a POX5 probe revealed the presence of a 6.1 Kb EcoR1 fragment not present in the wild-type (a representative of these transformants is designated as strain H51) This fragment is about 2.2 Kb larger than the wild-type POX5 EcoR1 fragment (3.9 Kb) and corresponds to the replacement of the wild-type POX5 locus with the POX5-URA3A disruption cassette. This 6.1 Kb EcoR1 fragment was also detected with a URA3A probe. However, hybridization to the POX5 probe also "uncovered" the presence of an additional wild-type copy of the POX5 gene (3.9 Kb) in each of these transformants. This EcoR1 hybridization pattern could reflect either a tandem integration of the disruption cassette into a haploid POX5 gene or a disruption of a single POX5 gene at a diploid locus. The more intense hybridization of the POX5 probe to the 3.9 Kb POX5 EcoR1 fragment in the wild-type suggested that there are normally two copies of the POX5 gene. To distinguish these possibilities, genomic DNA from the transformants was digested with NcoI and analyzed by Southern hybridization as described above. Since there are no internal NcoI sites within the POX5-URA3A disruption cassette, the fragment sizes generated by NcoI digestion depend upon the chromosomal location of the NcoI sites nearest the site of integration. Thus, tandem repeats resulting from single-crossover integration would appear as a single large fragment while a POX5 gene disruption at a diploid locus would yield two fragments. The hybridization to a POX5 gene probe demonstrated the presence of two NcoI fragments in each of the transformants while only one was detected, with greater hybridization intensity, in the wild-type. Only the larger of the two fragments in each transformant was detected by hybridization to a URA3A gene probe and corresponds in size to that expected for the replacement of the chromosomal POX5 gene with the POX5-URA3A disruption cassette. Thus, the NcoI hybridization pattern clearly established the disruption in these transformants, designated as H51 (pox5:URA3A/POX5/POX4A/POX4B), of a single copy of the POX5 gene at a normally diploid locus. Only one of the two POX5 genes has been functionally inactivated as the result of the gene disruption. Selective disruption of the remaining POX5 gene is necessary to functionally inactivate POX5 activity. All of the 11 transformants analyzed contained the expected POX5 gene disruption at the chromosomal POX5 locus. None of the Ura+ transformants were recovered as the result of integration at the chromosomal URA3A locus.

EXAMPLE 14

Disruption of the C. tropicalis Chromosomal POX4 Gene

C. tropicalis strain SU-2 (ATCC 20913) spheroplasts were transformed to uracil prototrophy with 10 ug of EcoR1 digested pKD3-URA3A as described in Example 4. Approximately 160 mitotically stable Ura+ transformants were recovered. All demonstrated the ability to utilize either dodecane or methyl laurate for growth. Nine Ura+ transformants were screened by Southern hybridization for site-specific gene disruption as previously described. Hybridization of EcoR1 digested genomic DNA from six of these transformants to a POX4 probe revealed the presence of a 13 Kb EcoR1 fragment not present in the wild-type (a representative of these transformants is designated as strain H41). This fragment is about 2.2 Kb larger than the wild-type POX4 EcoR1 fragment and corresponds to the replacement of the wild-type POX4 locus with the POX4-URA 3A disruption cassette. This 13 Kb EcoR1 fragment was also detected with a URA3A probe in strain H41 but not in strain SU-2. However, hybridization to the POX4 probe also "uncovered" the presence of an additional wild-type copy of the POX4 gene in each of these transformants thus indicating that C. tropicalis is also diploid at the POX4 locus. Hybridization of HpaI digested genomic DNA to a POX4 probe indicated that the two chromosomes are heterozygous at this restriction site, thus distinguishing the chromosome into which the transforming DNA had integrated. By comparing the EcoR1 and HpaI hybridization patterns, it was determined that, of the nine Ura+ transformants analyzed, two contained precise gene disruption of one POX4 gene, three contained a single crossover integration into one POX4 gene (of which one was a tandem multiple integration), and four contained both a single crossover integration and a gene disruption into one or both chromosomes. The strains containing only precise disruption of one of the POX4 genes were designated as H41 (POX5/POX5/pox4A:URA3A/POX4B).

EXAMPLE 15

Regeneration of the URA3 Selectable Marker System (A) Selection of Uracil Auxotrophs Resulting From Spontaneous Mutation Within The URA3A Selectable Marker.

*C. tropicalis* SU-2 (Ura−) and H51 (Ura+) were tested for growth in media containing various concentrations of 5-fluoroorotic acid (5-FOA), an analogue of a uracil pathway intermediate which is toxic to Ura+ cells. Both strains were grown to mid-log phase in YEPD medium (2% Bacto-peptone, 2% glucose, 1% Bacto-Yeast Extract) and were plated at various dilutions onto FOA medium (Boeke et al., [1984] Molec. Gen. Genet. 197; p345-346) or YEPD medium.

*C. tropicalis* SU-2 demonstrated 71.6%, 50.3% and 14.8% survival in the presence of 500, 750 and 1000 ug/ml 5-FOA, respectively. Under comparable conditions, the Ura+ transformants (H51) demonstrated survival rates of less than $3.6 \times 10^{-6}$. Concentrations of less than 500 ug/ml were found to permit the growth of spontaneous 5-FOA resistant mutants that retained the Ura+ phenotype. Thus, selection in the presence of 750 ug/ml 5FOA permits identification of isolates which have a non-functional URA3A marker.

EXAMPLE 16

Regeneration of the URA3 Selectable Marker System (B) Directed Chromosomal Deletion Plasmid pCU3dKpnI was constructed by progressive Bal31 deletion from the unique KpnI site within the URA3A gene. For these constructions, 10 ug aliquots of plasmid pCU3 were linearized by digestion with KpnI restriction endonuclease and were subsequently partially digested with Bal31 nuclease (0.05 U/ug for 5,10,20 or 30 min at 30° C.). Following treatment with DNA polymerase Klenow fragment, the plasmids were recircularized by ligation at low DNA concentration (0.05 ug/ul). The ligation mixtures were used to transform *E. coli* HB101 to ampicillin resistance or were digested with EcoR1 and PstI for direct transformation of *C. tropicalis* H51. Three plasmids containing a deletion of the KpnI site and extending toward the BglII sites were recovered from the ampicillin resistant *E. coli* transformants. The deletion cassettes derived from these plasmids can be used to generate relatively small URA3A deletions (bp) while maintaining large stretches of URA3A homology (Kb), and are liberated by digestion of the plasmids with EcoR1 and PstI. Strain H51 was transformed with 20 ug of EcoR1/PstI digested pCU3dKpnI, previously purified and characterized as containing a 50 bp deletion spanning the URA3A KpnI site, by either the LiCl procedure (Ito et al., [1983] J. Bacteriol.153; 163-168) or the spheroplast procedure. The spheroplast transformation was performed as previously described, except that the spheroplasts were regenerated on the surface of the regeneration medium to facilitate their recovery for subsequent screening. The Ura+ isolates were phenotypically identified following nystatin enrichment (described below) and, in some cases, selection for 5-FOA resistance. The cells from the surface of the transformation plates were pooled by washing with sterile YEPD and were inoculated to a starting $A_{600}$ of 0.1 in YEPD and cultured at 30° C. until an $A_{600}$ Of 0.4 was reached. The cells were harvested by centrifugation (5000×g, 5 min) and inoculated into 100 ml of yeast carbon base (YCB; 11 g/L; Difco) in a sterile 500 ml flask. The culture was shaken at 200 rpm for 21 hours at 30° C. The cells were then centrifuged (5000×g, 5 min), washed once with sterile distilled water and resuspended in 100 ml of minimal medium (yeast nitrogen base 6.7 g/L, dextrose 20 g/L) in 500 ml flasks. The cells were incubated with shaking (200 rpm) at 30° C. for 7 hours. Then, nystatin (50,000 units/ml stock solution in methanol; Sigma #N3503) was added at a final concentration of 35 units/ml and the cells incubated for 35 minutes at 30° C. with shaking (200 rpm). The culture was washed twice with sterile distilled water and resuspended in 10 ml of sterile distilled water. Nystatin-treated cells (0.1 ml aliquots) were plated onto selection plates (YNB 6.7 g/L, dextrose 20 g/L, agar 20 g/L, uracil 50 mg/L, uridine 150 mg/L, uridine 5-phosphate 150 mg/L, 5-fluoroorotic acid 750 mg/L). The plates were incubated for up to two weeks at 30° C., at which time the colonies which grew on the plates were picked with sterile toothpicks and plated onto a second set of selection plates prepared as before. Incubation was for four days at 30° C. The isolates were then transferred to minimal medium plates with or without added uracil. Colonies which could not grow in the absence of uracil were taken for further analysis. Characterization of 25 Ura-isolates recovered from the transformation of H51 spheroplasts with pCU3dKpnI (containing a 50 bp URA3A deletion with 2.4 Kb flanking URA3A homology) by Southern hybridization of EcoR1 digested genomic DNA to a POX5 probe showed 13 of the isolates to contain the expected deletion within the disrupted POX5 gene. These strains were designated as H51dKpn (pox5:dura3A/POX5/POX4A/POX4B). The remaining isolates were representative of mitotic recombinants. The 50 bp chromosomal deletion flanking the URA3A KpnI site in H51dKpn was further confirmed by Southern hybridization of KpnI digested genomic DNA to POX5 and URA3A gene probes. As expected, the 7.1 Kb and 1.4 Kb KIpnI fragments of H51 detected with the URA3A probe were replaced by an 8.5 Kb KpnI fragment in H51dKpn. The reversion frequencies of several independent H51dKpn isolates were all $<1 \times 10^{-8}$.

EXAMPLE 17

Regeneration of the URA3 Selectable Marker System

C. Spontaneous Mutation within the URA3A Selectable Marker: Construction of Strain H53 (pox5:ura3A/pox5:URA3A/POX4A/POX4B)

Strain H53 (pox5:ura3A/pox5:URA3A/POX4A/POX4B) was isolated following transformation of a Ura− derivative of H51 (H51Ura−) with the POX5-URA3A disruption cassette from pKD1-URA3A to Ura+ as follows: Several spontaneous 5-FOA resistant isolates recovered from H51 in the absence of transforming DNA were found to be identical to H51 in their POX5 EcoR1 hybridization pattern but were phenotypically Ura−. The strains were designated H51Ura− (pox5:ura3A/POX5/POX4A/POX4B). It was reasoned that these derivatives might represent spontaneous point mutations within the URA3A gene at the disrupted POX5 locus and could thus be retransformed with the URA3A selectable marker or, in particular, with the POX5-URA3A disruption cassette to effectively inactivate the remaining functional POX5 gene. Therefore, 20 isolates with a Ura− phenotype and an H51 hybridization pattern were separately transformed to Ura+ with 10 ug of EcoR1 digested pKD1-URA3A. Three strains had reversion frequencies (to a Ura+ phenotype) which were low enough to permit easy identification of Ura+ transformants. Characterization of 28 Ura+ transformants from these three strains by Southern hybridization of EcoR1 digested genomic DNA to a POX5 probe identified 9 transformants which demonstrated the sole presence of a 6.1 Kb EcoR1 fragment with twice the hybridization intensity of H51. These transformants, which have been designated H53 (pox5:ura3A/pox5:URA3A/POX4A/POX4B), represent disruption of both copies of the POX5 gene. These strains are capable of growth on dodecane as the sole carbon source. The remaining transformants were identical to H51 and may have resulted from either reversion, gene conversion or by gene replacement at the original disrupted POX5 gene.

EXAMPLE 18

Development of Strain H534 (pox5:ura3A/pox5:ura3A/pox4A:URA3A/POX4B)

This strain, which has both copies of POX5 and one copy of POX4 disrupted was developed by the procedures described above. Ura⁻ derivatives of H53 (H53Ura⁻:pox5:ura3A/p5xS:ura3A/POX4A/POX4B) were isolated and characterized as described above and then transformed to Ura⁺ with the POX4 disruption cassette from pKD3-URA3A. Fifty percent of the Ura+ transformants screened by Southern hybridization to both POX4 and POX5 probes had the expected POX4 disruption. FOA$^r$, Ura⁻ derivatives with low URA⁺ reversion frequency were obtained from this mutant (designated H534Ura−;pox5:ura3A/pox5:ura3A/pox4A:ura3A/POX4B) in preparation for disruption of the remaining functional POX4 gene.

EXAMPLE 19

Development of Strain H45 (pox5:URA3A/POXS/pox4A:ura3A/POX4B)

This strain, which has one copy of both the POX4 and POX5 genes disrupted, was also developed by the procedures described above. Several FOA resistant, Ura⁻ derivatives from Strain H41 which demonstrated Ura⁺ reversion frequencies <2×10⁻⁷ were isolated and screened by Southern hybridization to a POX4 probe for an EcoR1 restriction pattern identical to H41. Several candidates, presumably containing a point mutation within the URA3A gene at the disrupted POX4 locus, were recovered and designated as H41Ura−(POX5/POX5/pox4A:ura3A/POX4B).

Strain H45 was isolated following transformation of H41ura− with the POX5 disruption cassette from pKD1-URA3A. All Ura+ transformants analyzed by Southern hybridization to a POX5 probe contained the expected POX5 disruption.

EXAMPLE 20

Development of Strain H41B (POX5/POX5/POX4A/pox4B:URA3A)

To inactivate POX4B, SU-2 was transformed to Ura+ with a truncated POX4A disruption cassette lacking non-homologous flanking sequences, depending primarily on homologous sequences within the structural gene to direct the mutagenesis. To prepare POX4A for this transformation, the usual 8.3 Kb EcoR1 disruption cassette from pKD3URA3 was digested with Bal31 and SalI to generate fragments of approximately 5 Kb and comprised mostly of structural gene sequences flanking the URA3A selectable marker. This DNA was used to transform SU-2 to Ura+. One of the 20 SU-2 transformants screened by Southern hybridization of HpaI digested genomic DNA to a POX4A probe had the expected POX4B disruption. This strain, designated as H41B (POX5/POX5/POX4A/pox4B:URA3A), was confirmed by Southern hybridization of EcoR1 or HpaI digested genomic DNA to POX4A, URA3A and pBR322 probes. 5FOA-resistant, uracil requiring derivatives from H41B were prepared for the construction of the double POX4 mutant, H43.

EXAMPLE 21

Development of Strain H43 (POX5/POX5/pox4A:URA3A/pox4B:ura3A)

This strain, which contains a disruption of both POX4 genes, was isolated following transformation of H41BUra³¹ to Ura³⁰ with the POX4A disruption cassette from pKD3-URA3A. Seven of the 20 Ura⁺ transformants screened by Southern hybridization of HpaI digested genomic DNA to a POX4A probe had the expected construction.

EXAMPLE 22

Development of Strain H534B (pox5:ura3A/pox5:ura3A/POX4A/pox4B:URA3A)

This strain, which contains a disruption of both POX5 genes as well as the POX4B gene, was developed as described above. This strain was isolated following transformation of a uracil-requiring derivative of H53 (H53Ura⁻) with a truncated POX4A-based disruption cassette in order to target the POX4B gene. Two of the 23 URA⁺ transformants screened by Southern hybridization of SacI digested genomic DNA to a POX4A probe had the expected POX4B gene disruption. The EcoR1 hybridization pattern of H534B is identical to H534.

EXAMPLE 23

Development of Strain H435 (pox5:URA3A/POX5/pox4A:ura3A/pox4B:ura3A)

This strain, which has both POX4 genes and one POX5 gene disrupted, was constructed by transformation of a uracil-requiring derivative of H43 (H43Ura⁻) with the POX5 disruption cassette from EcoR1 digested pKD1-URA3A. Eight of the 10 Ura⁺ transformants screened by Southern hybridization of EcoR1 digested genomic DNA to a POX5 probe had the expected construction.

EXAMPLE 24

Development of Strain H5343 (pox5:ura3A/pox5:ura3A/pox4A:ura3A/pox4B:URA3A)

This strain, in which all POX4 and POX5 genes have been inactivated, was isolated following transformation of a uracil-requiring derivative of H534 (H534Ura−) to Ura+ with the truncated POX4A-based disruption cassette from pKD3-URA3A. Three of the 100 transformants screened by Southern hybridization of SacI digested genomic DNA to a POX4A probe contained a disruption of the POX4B gene. Further evaluation of H5343 by Southern hybridization to a POX5 probe confirmed retention of all previous disruptions. Unlike all previous mutants in the lineage, H5343 can no longer utilize dodecane or methyl laurate as a sole carbon source for growth.

EXAMPLE 25

Construction of plasmid pCU2dSacI

A 5.8 kb DNA fragment containing the URA3A gene was obtained from the YEp13-based *C. tropicalis* genomic library plasmid, pCU1 (ATCC 67867). To facilitate restriction enzyme mapping of this fragment, most of the fragment was subcloned into pUC19 which is a small (2,686 basepair) pBR322- and M13mp19-based cloning vector containing a multiple cloning site, or polylinker (Yanisch-Perron, C. et al., Gene (1985) 33:103–119). To construct this plasmid, a 6.2 kb EcoRI fragment from pCU1 containing mostly C. tropicalis DNA was inserted into the EcoRI site of pUC19, to produce plasmid pCU2. One end of the subcloned fragment contained 377 base pairs of YEp13, and the other stopped at an EcoRI site located approximately 50 base pairs from the right hand BamHI-Sau3AI junction. To construct pCU2dSacI, the 2.8 Kb EcoR1/SacI restriction fragment from pCU2 was subcloned into the EcoR1/.SacI sites in the polylinker sequences of pUC19.

EXAMPLE 26

Construction of Plasmid pKD1dBamH1.

The C. tropicalis POX5 gene was first subcloned on a 3.9 Kb EcoR1 restriction fragment from plasmid pC50 (obtained from Prof. T. Kamiryo, Hiroshima University, Hiroshima, Japan) into the unique EcoR1 site of pBR322 by standard procedures (Maniatis et al, Molecular Cloning: A Laboratory Manual, Cold Spring Harbor, 1982) to generate the plasmid designated pKD1. To facilitate in-vitro disruption of the subcloned POX5 gene, by insertional inactivation with a selectable marker gene such as the C. tropicalis URA3A gene, by subcloning into the unique POX5 BamH1 site (position #1178), an interfering BamH1 site located in the tetracycline resistance gene of pBR322 was destroyed by partial digestion of pKD1 with BamH1 restriction endonuclease followed by filling-in of the cohesive ends with DNA polymerase and intramolecular blunt-end ligation. The ligated DNA was used to transform E. coli HB101 to ampicillin resistance and an analysis of the plasmids from 5 ampicillin resistant, tetracycline sensitive transformants showed that two of them contained the expected construction. BamH1 digestion of the plasmid, designated pKD1dBamH1, yields a single linear restriction fragment suitable for the subcloning of the C. tropicalis URA3A gene into the unique POX5 BamH1 site.

EXAMPLE 27

Construction of Plasmid pKD3dBamH1

The C. tropicalis POX4 gene was first subcloned on a 6.6 Kb HindIII restriction fragment from plasmid pC1 (obtained from Prof. T. Kamiryo, Hiroshima University, Hiroshima, Japan) into the unique HindIII site of pBR322 by standard procedures (Maniatis et al, Molecular Cloning: A Laboratory Manual, Cold Spring Harbor, 1982) to generate the plasmid designated pKD3. To facilitate in-vitro disruption of the subcloned POX4 gene by insertional inactivation with a selectable marker gene, in particular the C. tropicalis URA3A gene, an interfering BamH1 site located in the tetracycline resistance gene of pBR322 was destroyed. This was accomplished by partial digestion of pKD3 with BamH1 restriction endonuclease followed by filling-in of the cohesive ends with DNA polymerase (Klenow) and intramolecular blunt-end ligation. The ligated DNA was used to transform E. coli HB101 to ampicillin resistance and an analysis of the plasmids from ampicillin resistant, tetracycline sensitive transformants yielded the desired construction. BamH1 digestion of the plasmid, designated pKD3dBamH1, yields a single linear restriction fragment suitable for the subcloning of the C. tropicalis URA3A gene into the unique POX4 gene.

DEPOSIT OF MICROORGANISMS

Living cultures of Candida Tropicalis AR40 designated ATCC 20987, plasmid pDS-1 in E. Coli designated ATCC 68247, plasmid pTS-1 in E. Coli designated ATCC 68248, strain Candida Tropicalis SU-2 (ATCC 20913), and strain Candida Tropicalis H5343 (ATCC 20962) have been deposited with American Type Culture Collection, 12301 Parklawn Drive, Rockville, Md. 20852 under the Budapest Treaty on the International Recognition of the Deposit of Microorganisms for the purposes of patent procedure.

What is claimed is:

1. A process for increasing the omega-hydroxylase activity in C. tropicalis comprising introducing into the genome of said C. tropicalis one or more copies of a P450ALK or P450RED gene or a combination thereof.

2. The process of claim 1 wherein said C. tropicalis is SU-2.

3. The process of claim 1 wherein said C. tropicalis is H41.

4. The process of claim 1 wherein said C. tropicalis is H41B.

5. The process of claim 1 wherein said C. tropicalis is H43.

6. The process of claim 1 wherein said C. tropicalis is H51.

7. The process of claim 1 wherein said C. tropicalis is H53.

8. The process of claim 1 wherein said C. tropicalis is H45.

9. The process of claim 1 wherein said C. tropicalis is H534 or H534B.

10. The process of claim 1 wherein said C. tropicalis is H435.

11. The process of claim 1 wherein said C. tropicalis is H5343.

12. The process of claim 1 wherein said P450ALK gene is P450ALK1 or P450ALK2.

13. The process for increasing the omega-hydroxylase activity in C. tropicalis according to claim 1 wherein, after introducing into the genome of said C. tropicalis one or more copies of a P450ALK or P450RED gene or a combination thereof, the level of omega-hydroxylase activity is at least 0.206 percent lauric acid conversion/µg.

14. A transformed C. tropicalis host having an increased copy number of the P450ALK gene relative to the wild type strain wherein the chromosomal POX4A gene in said C. tropicalis host is disrupted through homologous recombination of said POX4A gene with a linear DNA fragment comprised of a URA3A selectable marker gene wherein said selectable marker gene is flanked on both ends by DNA sequences having homology to said POX4A gene.

15. The transformed host of claim 14 wherein said P450ALK gene is a P450ALK1 gene.

16. The transformed host of claim 14 wherein said P450ALK gene is a P450ALK2 gene.

17. A transformed C. tropicalis host having an increased copy number of the P450RED gene relative to the wild type strain wherein the chromosomal POX4A gene in said C. tropicalis host is disrupted through homologous recombination of said POX4A gene with a linear DNA fragment comprised of a URA3A selectable marker gene wherein said selectable marker gene is flanked on both ends by DNA sequences having homology to said POX4A gene.

18. A transformed C. tropicalis host having an increased copy number of both the P450ALK and P450RED genes relative to the wild type strain wherein the chromosomal POX4A gene in said C. tropicalis host is disrupted through homologous recombination of said POX4A gene with a linear DNA fragment comprised of a URA3A selectable marker gene wherein said selectable marker gene is flanked on both ends by DNA sequences having homology to said POX4A gene.

19. A transformed *C. tropicalis* host having an increased copy number of the P450ALK gene relative to the wild type strain wherein the chromosomal POX4B gene in said *C. tropicalis* host is disrupted through homologous recombination of said POX4B gene with a linear DNA fragment comprised of a URA3A selectable marker gene wherein said selectable marker gene is flanked on both ends by DNA sequences having homology to said POX4B gene.

20. The transformed host of claim 19 wherein said P450ALK gene is a P450ALK1 gene.

21. The transformed host of claim 19 wherein said P450ALK gene is a P450ALK2 gene.

22. A transformed *C. tropicalis* host having an increased copy number of the P450RED gene relative to the wild type strain wherein the chromosomal POX4B gene in said *C. tropicalis* host is disrupted through homologous recombination of said POX4B gene with a linear DNA fragment comprised of a URA3A selectable marker gene wherein said selectable marker gene is flanked on both ends by DNA sequences having homology to said POX4B gene.

23. A transformed *C. tropicalis* host having an increased copy number of both the P450ALK and P450RED genes relative to the wild type strain wherein the chromosomal POX4B gene in said *C. tropicalis* host is disrupted through homologous recombination of said POX4B gene with a linear DNA fragment comprised of a URA3A selectable marker gene wherein said selectable marker gene is flanked on both ends by DNA sequences having homology to said POX4B gene.

24. A transformed *C. tropicalis* host having an increasd copy number of the P450ALK gene relative to the wild type strain wherein one of the chromosomal POX5 genes in said *C. tropicalis* host is disrupted through homologous recombination of said POX5 gene with a linear DNA fragment comprised of a URA3A selectable marker gene wherein said selectable marker gene is flanked on both ends by DNA sequences having homology to said POX5 gene.

25. The transformed host of claim 24 wherein said P450ALK gene is a P450ALK1 gene.

26. The transformed host of claim 24 wherein said P450ALK gene is a P450ALK2 gene.

27. A transformed *C. tropicalis* host having an increased copy number of the P450RED gene relative to the wild type strain wherein one of the chromosomal POX5 genes in said *C. tropicalis* host is disrupted through homologous recombination of said POX5 gene with a linear DNA fragment comprised of a URA3A selectable marker gene wherein said selectable marker gene is flanked on both ends by DNA sequences having homology to said POX5 gene.

28. A transformed *C. tropicalis* host having an increased copy number of both the P450ALK and P450RED genes relative to the wild type strain wherein one of the chromosomal POX5 genes in said *C. tropicalis* host is disrupted through homologous recombination of said POX5 gene with a linear DNA fragment comprised of a URA3A selectable marker gene wherein said selectable marker gene is flanked on both ends by DNA sequences having homology to said POX5 gene.

29. A transformed *C. tropicalis* host having an increased copy number of the P450ALK gene relative to the wild type strain wherein the chromosomal POX4A and one of the chromosomal POX5 genes in said *C. tropicalis* host are disrupted through homologous recombination of each of said POX4A and POX5 genes with a linear DNA fragment comprised of a URA3A selectable marker gene wherein said selectable marker gene is flanked on both ends by DNA sequences having homology to said POX4A or one of said POX5 genes respectively.

30. The transformed host of claim 29 wherein said P450ALK gene is a P450ALK1 gene.

31. The transformed host of claim 29 wherein said P450ALK gene is a P450ALK2 gene.

32. A transformed *C. tropicalis* host having an increased copy number of the P450RED gene relative to the wild type strain wherein the chromosomal POX4A and one of the chromosomal POX5 genes in said *C. tropicalis* host are disrupted through homologous recombination of each of said POX4A and POX5 genes with a linear DNA fragment comprised of a URA3A selectable marker gene wherein said selectable marker gene is flanked on both ends by DNA sequences having homology to said POX4A or one of said POX5 genes respectively.

33. A transformed *C. tropicalis* host having an increased copy number of both the P450ALK and P450RED genes relative to the wild type strain wherein the chromosomal POX4A and one of the chromosomal POX5 genes in said *C. tropicalis* host are disrupted through homologous recombination of each of said POX4A and POX5 genes with a linear DNA fragment comprised of a URA3A selectable marker gene wherein said selectable marker gene is flanked on both ends by DNA sequences having homology to said POX4A or one of said POX5 genes respectively.

34. A transformed *C. tropicalis* host having an increased copy number of the P450ALK gene relative to the wild type strain wherein the chromosomal POX4A and POX4B genes in said *C. tropicalis* host are disrupted through homologous recombination of each of said POX4A and POX4B genes with a linear DNA fragment comprised of a URA3A selectable marker gene wherein said selectable marker gene is flanked on both ends by DNA sequences having homology to said POX4A or POX4B gene respectively.

35. The transformed host of claim 34 wherein said P450ALK gene is a P450ALK1 gene.

36. The transformed host of claim 34 wherein said P450ALK gene is a P450ALK2 gene.

37. A transformed *C. tropicalis* host having an increased copy number of the P450RED gene relative to the wild type strain wherein the chromosomal POX4A and POX4B genes in said *C. tropicalis* host are disrupted through homologous recombination of each of said POX4A and POX4B genes with a linear DNA fragment comprised of a URA3A selectable marker gene wherein said selectable marker gene is flanked on both ends by DNA sequences having homology to said POX4A or POX4B gene respectively.

38. A transformed *C. tropicalis* host having an increased copy number of the P450ALK and P450RED gene relative to the wild type strain wherein the chromosomal POX4A and POX4B genes in said *C. tropicalis* host are disrupted through homologous recombination of each of said POX4A and POX4B genes with a linear DNA fragment comprised of a URA3A selectable marker gene wherein said selectable marker gene is flanked on both ends by DNA sequences having homology to said POX4A or POX4B gene respectively.

39. A transformed *C. tropicalis* host having an increased copy number of the P450ALK gene relative to the wild type strain wherein both copies of the chromosomal POX5 genes in said *C. tropicalis* host are disrupted through homologous recombination of each of said POX5 genes with a linear DNA fragment comprised of a URA3A selectable marker gene wherein said selectable marker gene is flanked on both ends by DNA sequences having homology to both of said POX5 genes.

40. The transformed host of claim 39 wherein said P450ALK gene is a P450ALK1 gene.

41. The transformed host of claim 39 wherein said P450ALK gene is a P450ALK2 gene.

42. A transformed C. tropicalis host having an increased copy number of the P450RED gene relative to the wild type strain wherein both copies of the chromosomal POX5 genes in said C. tropicalis host are disrupted through homologous recombination of each of said POX5 genes with a linear DNA fragment comprised of a URA3A selectable marker gene wherein said selectable marker gene is flanked on both ends by DNA sequences having homology to both of said POX5 genes.

43. A transformed C. tropicalis host having an increased copy number of the P450ALK and P450RED genes relative to the wild type strain wherein both copies of the chromosomal POX5 genes in said C. tropicalis host are disrupted through homologous recombination of each of said POX5 genes with a linear DNA fragment comprised of a URA3A selectable marker gene wherein said selectable marker gene is flanked on both ends by DNA sequences having homology to both of said POX5 genes.

44. A transformed C. tropicalis host having an increased copy number of the P450ALK gene relative to the wild type strain wherein both copies of the chromosomal POX5 gene and the POX4A gene in said C. tropicalis host are disrupted through homologous recombination of each of both of said POX5 genes and said POX4A gene with a linear DNA fragment comprised of a URA3A selectable marker gene wherein said selectable marker gene is flanked on both ends by DNA sequences having homology to both of said POX5 genes or said POX4A gene respectively.

45. The transformed host of claim 44 wherein said P450ALK gene is a P450ALK1 gene.

46. The transformed host of claim 44 wherein said P450ALK gene is a P450ALK2 gene.

47. A transformed C. tropicalis host having an increased copy number of the P450RED gene relative to the wild type strain wherein both copies of the chromosomal POX5 genes and the POX4A gene in said C. tropicalis host are disrupted through homologous recombination of each of both of said POX5 genes and said POX4A gene with a linear DNA fragment comprised of a URA3A selectable marker gene wherein said selectable marker gene is flanked on both ends by DNA sequences having homology to both of said POX5 genes or said POX4A gene respectively.

48. A transformed C. tropicalis host having an increased copy number of both the P450ALK and P450RED genes relative to the wild type strain wherein both copies of the chromosomal POX5 gene and the POX4A gene in said C. tropicalis host are disrupted through homologous recombination of each of both of said POX5 genes and said POX4A gene with a linear DNA fragment comprised of a URA3A selectable marker gene wherein said selectable marker gene is flanked on both ends by DNA sequences having homology to both of said POX5 genes or said POX4A gene respectively.

49. A transformed C. tropicalis host having an increased copy number of the P450ALK gene relative to the wild type strain wherein both copies of the chromosomal POX5 gene and the POX4B gene in said C. tropicalis host are disrupted through homologous recombination of each of said POX5 genes and said POX4B gene with a linear DNA fragment comprised of a URA3A selectable marker gene wherein said selectable marker gene is flanked on both ends by DNA sequences having homology to both of said POX5 genes or said POX4B gene respectively.

50. The transformed host of claim 49 wherein said P450ALK gene is a P450ALK1 gene.

51. The transformed host of claim 49 wherein said P450ALK gene is a P450ALK2 gene.

52. A transformed C. tropicalis host having an increased copy number of the P450RED gene relative to the wild type strain wherein both copies of the chromosomal POX5 gene and the POX4B gene in said C. tropicalis host are disrupted through homologous recombination of each of said POX5 genes and said POX4B gene with a linear DNA fragment comprised of a URA3A selectable marker gene wherein said selectable marker gene is flanked on both ends by DNA sequences having homology to both of said POX5 genes or said POX4B gene respectively.

53. A transformed C. tropicalis host having an increased copy number of both the P450ALK and P450RED genes relative to the wild type strain wherein both copies of the chromosomal POX5 gene and the POX4B gene in said C. tropicalis host are disrupted through homologous recombination of each of said POX5 genes and said POX4B gene with a linear DNA fragment comprised of a URA3A selectable marker gene wherein said selectable marker gene is flanked on both ends by DNA sequences having homology to both of said POX5 genes or said POX4B gene respectively.

54. A transformed C. tropicalis host having an increased copy number of the P450ALK gene relative to the wild type strain wherein one of the chromosomal POX5 genes and the POX4A and POX4B genes in said C. tropicalis host are disrupted through homologous recombination of each of said POX5 genes, said POX4A gene, and said POX4B gene with a linear DNA fragment comprised of a URA3A selectable marker gene wherein said selectable marker gene is flanked on both ends by DNA sequences having homology to said POX5 gene, said POX4A, or said POX4B gene respectively.

55. The transformed host of claim 54 wherein said P450ALK gene is a P450ALK1 gene.

56. The transformed host of claim 54 wherein said P450ALK gene is a P450ALK2 gene.

57. A transformed C. tropicalis host having an increased copy number of the P450RED gene relative to the wild type strain wherein one of the chromosomal POX5 genes and the POX4A and POX4B genes in said C. tropicalis host are disrupted through homologous recombination of said POX5 gene, said POX4A, and said POX4B gene each with a linear DNA fragment comprised of a URA3A selectable marker gene wherein said selectable marker gene is flanked on both ends by DNA sequences having homology to said POX5 gene, said POX4A, or said POX4B gene respectively.

58. A transformed C. tropicalis host having an increased copy number of both the P450ALK and P450RED genes relative to the wild type strain wherein one of the chromosomal POX5 genes and the POX4A and POX4B genes in said C. tropicalis host are disrupted through homologous recombination of said POX5 gene, said POX4A, and said POX4B gene each with a linear DNA fragment comprised of a URA3A selectable marker gene wherein said selectable marker gene is flanked on both ends by DNA sequences having homology to said POX5 gene, said POX4A, or said POX4B gene respectively.

59. A transformed C. tropicalis host having an increased copy number of the P450ALK gene relative to the wild type strain wherein both copies of the chromosomal POX5 gene and the POX4A and POX4B genes in said *C. tropicalis* host are disrupted through homologous recombination of each of both of said POX5 genes, said POX4A, and said POX4B gene with a linear DNA fragment comprised of a URA3A selectable marker gene wherein said selectable marker gene is flanked on both ends by DNA sequences having homology to both of said POX5 genes, said POX4A, or said POX4B gene respectively.

60. The transformed host of claim 59 wherein said P450ALK gene is a P450ALK1 gene.

61. The transformed host of claim 59 wherein said P450ALK gene is a P450ALK2 gene.

62. A transformed *C. tropicalis* host having an increased copy number of the P450RED gene relative to the wild type strain wherein both copies of the chromosomal POX5 gene and the and POX4A and POX4B genes in said *C. tropicalis* host are disrupted through homologous recombination of each of both of said POX5 genes, said POX4A, and said POX4B gene with a linear DNA fragment comprised of a URA3A selectable marker gene wherein said selectable marker gene is flanked on both ends by DNA sequences having homology to both of said POX5 genes, said POX4A, or said POX4B gene respectively.

63. A transformed *C. tropicalis* host having an increased copy number of both the P450ALK and P450RED genes relative to the wild type strain wherein both copies of the chromosomal POX5 gene and the POX4A and POX4B genes in said *C. tropicalis* host are disrupted through homologous recombination of each of both of said POX5 genes, said POX4A, and said POX4B gene with a linear DNA fragment comprised of a URA3A selectable marker gene wherein said selectable marker gene is flanked on both ends by DNA sequences having homology to both of said POX5 genes, said POX4A, or said POX4B gene respectively.

64. A transformed *C. tropicalis* host having an increased copy number of the P450ALK gene relative to the wild type strain wherein the chromosomal POX4B and one of the chromosomal POX5 genes in said *C. tropicalis* host are disrupted through homologous recombination of each of said POX4B and POX5 genes with a linear DNA fragment comprised of a URA3A selectable marker gene wherein said selectable marker gene is flanked on both ends by DNA sequences having homology to said POX4B or one of said POX5 genes respectively.

65. The transformed host of claim 64 wherein said P450ALK gene is a P450ALK1 gene.

66. The transformed host of claim 64 wherein said P450ALK gene is a P450ALK2 gene.

67. A transformed *C. tropicalis* host having an increased copy number of the P450RED gene relative to the wild type strain wherein the chromosomal POX4B and one of the chromosomal POX5 genes in said *C. tropicalis* host are disrupted through homologous recombination of each of said POX4B and POX5 genes with a linear DNA fragment comprised of a URA3A selectable marker gene wherein said selectable marker gene is flanked on both ends by DNA sequences having homology to said POX4B or one of said POX5 genes respectively.

68. A transformed *C. tropicalis* host having an increased copy number of both the P450ALK and P450RED genes relative to the wild type strain wherein the chromosomal POX4B and one of the chromosomal POX5 genes in said *C. tropicalis* host are disrupted through homologous recombination of each of said POX4B and POX5 genes with a linear DNA fragment comprised of a URA3A selectable marker gene wherein said selectable marker gene is flanked on both ends by DNA sequences having homology to said POX4B or one of said POX5 genes respectively.

69. A transformed *C. tropicalis* host having an increased copy number of a P450 gene selected from the group consisting of P450ALK, P450RED and combinations thereof relative to a wild type *C. tropicalis* strain wherein the level of omega-hydroxylase activity of the transformed *C. tropicalis* host is at least 0.206 percent lauric acid conversion/µg.

70. The transformed *C. tropicalis* host according to the claim 69 wherein the P450 gene is P450ALK.

71. The transformed *C. tropicalis* host according to claim 69 wherein the P450 gene is P450RED.

72. The transformed *C. tropicalis* host according to claim 69 further comprising a disrupted gene selected from the group consisting of POX4A, POX4B, POX 5 and combinations thereof.

73. The transformed *C. tropicalis* host according to claim 70 wherein the P450ALK gene is selected from the group consisting of P450ALK1, P450ALK2 and combinations thereof.

74. A transformed *C. tropicalis* host having an increased copy number of a P450RED gene relative to the wild type *C. tropicalis* strain wherein the omega-hydroxylase activity of the transformed *C. tropicalis* host is increased relative to the wild type *C. tropicalis* strain.

* * * * *